US011181509B2

(12) United States Patent
Kukita et al.

(10) Patent No.: US 11,181,509 B2
(45) Date of Patent: Nov. 23, 2021

(54) SENSING SENSOR

(71) Applicant: NIHON DEMPA KOGYO CO., LTD., Tokyo (JP)

(72) Inventors: Hiroyuki Kukita, Saitama (JP); Tsuyoshi Shiobara, Saitama (JP)

(73) Assignee: NIHON DEMPA KOGYO CO., LTD., Tokyo (JP)

(*) Notice: Subject to any disclaimer, the term of this patent is extended or adjusted under 35 U.S.C. 154(b) by 0 days.

(21) Appl. No.: 16/978,775

(22) PCT Filed: Mar. 6, 2019

(86) PCT No.: PCT/JP2019/008897
§ 371 (c)(1),
(2) Date: Sep. 8, 2020

(87) PCT Pub. No.: WO2019/172323
PCT Pub. Date: Sep. 12, 2019

(65) Prior Publication Data
US 2020/0408724 A1 Dec. 31, 2020

(30) Foreign Application Priority Data
Mar. 9, 2018 (JP) .............................. JP2018-043359

(51) Int. Cl.
*G01N 29/32* (2006.01)
*G01N 29/036* (2006.01)
G01N 33/00 (2006.01)

(52) U.S. Cl.
CPC ......... *G01N 29/326* (2013.01); *G01N 29/036* (2013.01); *G01N 29/323* (2013.01); *G01N 2033/0095* (2013.01)

(58) Field of Classification Search
CPC .. G01N 29/326; G01N 29/036; G01N 29/323; G01N 2033/0095; G01N 5/02
See application file for complete search history.

(56) References Cited

U.S. PATENT DOCUMENTS

2011/0223620 A1* 9/2011 Koyama ............ G01N 33/5438
435/7.31
2019/0265177 A1* 8/2019 Kukita ..................... H03B 5/32

FOREIGN PATENT DOCUMENTS

JP H1038784 2/1998
JP 2004264254 9/2004
(Continued)

OTHER PUBLICATIONS

"International Search Report (Form PCT/ISA/210)" of PCT/JP2019/008897, dated Jun. 4, 2019, with English translation thereof, pp. 1-4.

*Primary Examiner* — Xin Y Zhong
(74) *Attorney, Agent, or Firm* — JCIPRNET

(57) ABSTRACT

To provide a technique for expanding a measurement dynamic range and performing a stable detection in a sensing sensor using a crystal resonator. A spacer is disposed between an oscillator circuit that oscillates a crystal resonator and a base body that cools an oscillator circuit to a cryogenic temperature, and an oscillator circuit board includes a heater resistor that heats the oscillator circuit. Therefore, the temperature of the oscillator circuit that does not fall below a functional limit temperature and is a low temperature as much as possible can be provided. A negative resistance of the oscillator circuit can be increased, the measurement dynamic range can be expanded, and the crystal resonator can be stably oscillated.

5 Claims, 11 Drawing Sheets

(56) References Cited

FOREIGN PATENT DOCUMENTS

| JP | 2009182881 | 8/2009 |
| JP | 2011064599 | 3/2011 |
| JP | 2011203007 | 10/2011 |
| JP | 2012220454 | 11/2012 |
| JP | 2018080947 | 5/2018 |

\* cited by examiner

SENSING SENSOR

CROSS-REFERENCE TO RELATED APPLICATION

This application is a 371 application of the international PCT application serial no. PCT/JP2019/008897, filed on Mar. 6, 2019, which claims the priority benefits of Japan application no. 2018-043359, filed on Mar. 9, 2018. The entirety of each of the above-mentioned patent applications is hereby incorporated by reference herein and made a part of this specification.

TECHNICAL FIELD

The present invention relates to a sensing sensor that senses a sensing object from a frequency change of a piezoelectric resonator.

BACKGROUND ART

For example, as a sensing device using a sensing sensor configured to sense a material contained in a gas, there has been known a Quartz crystal microbalance (QCM) using a crystal resonator. As the QCM, for example, a crystal resonator is cooled down to a cryogenic temperature to attach a gas to the crystal resonator, and subsequently, the temperature of the crystal resonator is gradually increased to desorb the gas attached to the crystal resonator. There has been known a sensing device that measures an adhesion amount of the gas by measuring an amount of frequency variation before and after the gas desorption at this time, and specifies the component of the gas by measuring a temperature at which the gas desorbs.

Here, in the QCM, since crystal impedance (CI) of the crystal resonator increases due to the adhesion of the material, a negative resistance of an oscillator circuit is preferably increased as much as possible for increasing a dynamic range of the measurement as much as possible. Since a semiconductor used for the oscillator circuit has a characteristic of tending to increase the negative resistance by driving at low temperature, the oscillator circuit is preferably cooled as much as possible by heat cooling using liquid nitrogen and the like.

However, when the temperature of the oscillator circuit is decreased, for example, a silicon semiconductor element has a tendency that a carrier density decreases and an insulation property increases from the temperature around −110° C. Therefore, at an excessive cryogenic temperature, the semiconductor element, such as an integrated circuit (IC) for oscillation and a regulator, disposed to the oscillator circuit falls below a functional limit temperature, thus stopping the oscillator circuit. Accordingly, operating an oscillator circuit board at a temperature that does not fall below the functional limit temperature of the semiconductor and is a low temperature as much as possible provides the largest negative resistance and the wide measurement dynamic range, and ensures stable oscillation.

While Patent Document 1 discloses a technique to improve sensitivity of a sensing sensor by cooling a crystal resonator, it is not a technique for cooling the oscillator circuit. While Patent Document 2 discloses a technique to cool a substrate to which an IC chip is installed, it is not a technique for cooling to a cryogenic temperature, thus not being a technique considering a temperature characteristic of a semiconductor element.

CITATION LIST

Patent Document

Patent Document 1: Japanese Unexamined Patent Application Publication No. 2011-203007
Patent Document 2: Japanese Unexamined Patent Application Publication No. 2012-220454

SUMMARY OF THE INVENTION

Problems to be Solved

The present invention has been made under these circumstances, and it is an object of the present invention to provide a technique for expanding a measurement dynamic range and performing a stable detection in a sensing sensor that performs sensing by cooling/heating a piezoelectric resonator to desorb/attach a material.

Solutions to the Problems

A sensing sensor of the present invention attaches a substance to be sensed to a piezoelectric resonator, detaches the substance to be sensed by changing a temperature of the piezoelectric resonator, and senses the substance to be sensed based on a relationship between a change of an oscillation frequency and the temperature of the piezoelectric resonator. The substance to be sensed is a gas. The sensing sensor includes a base body, the piezoelectric resonator, a heating unit, a substrate, and a heat insulating portion. The base body is cooled by a liquid nitrogen. The piezoelectric resonator is cooled by the base body. The heating unit heats the piezoelectric resonator for changing the temperature of the piezoelectric resonator. The substrate is mounted to the base body. The substrate includes an oscillator circuit unit and a heater circuit thereon. The oscillator circuit unit oscillates the piezoelectric resonator. The heater circuit heats the oscillator circuit unit. The heat insulating portion is disposed between the base body and the oscillator circuit unit for avoiding a heat transfer of a cool heat from the base body to the oscillator circuit unit via the substrate.

Effects of the Invention

In the sensing sensor that attaches a substance to be sensed, which is a gas, to a piezoelectric resonator, detaches the substance to be sensed by changing a temperature of the piezoelectric resonator, and senses the substance to be sensed based on a relationship between a change of an oscillation frequency and the temperature of the piezoelectric resonator, the present invention is configured to cool the piezoelectric resonator by the base body cooled by the liquid nitrogen, and configured to heat the piezoelectric resonator by the heating unit. Furthermore, the base body includes the substrate on which the oscillator circuit unit that oscillates the piezoelectric resonator and the heater circuit that heats the oscillator circuit unit are included, and the heat insulating portion is disposed between the base body and the oscillator circuit unit. Therefore, the temperature of the oscillator circuit that does not fall below a functional limit temperature of the oscillator circuit and is a low temperature as much as possible can be provided. Accordingly, a negative resistance of the oscillator circuit can be increased, the measurement dynamic range can be expanded, and the stable oscillation can be performed.

DESCRIPTION OF EMBODIMENTS

Figure 1:
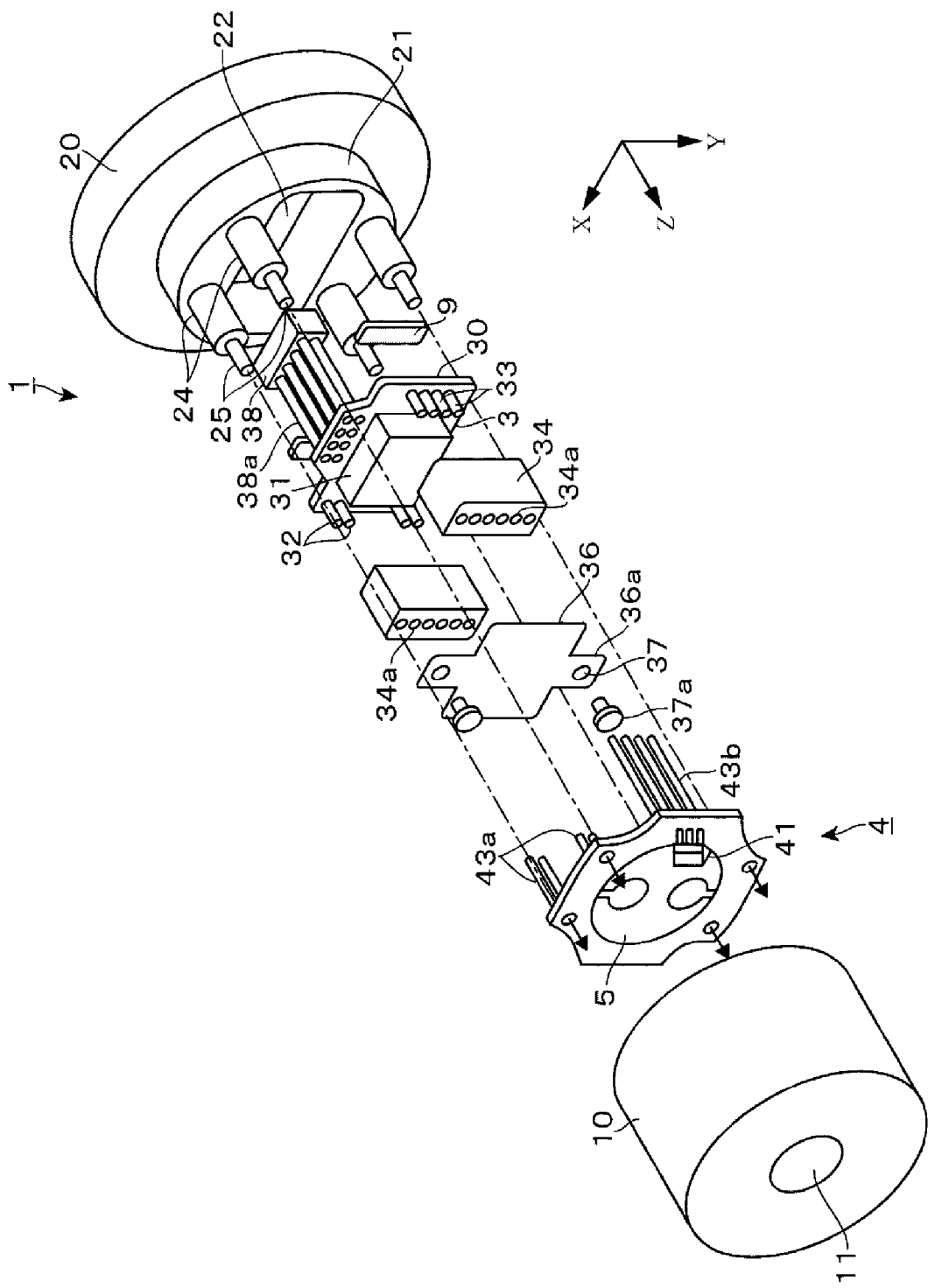
FIG. 1 is an exploded perspective view of a sensing sensor according to an embodiment of the present invention.
Figure 2:
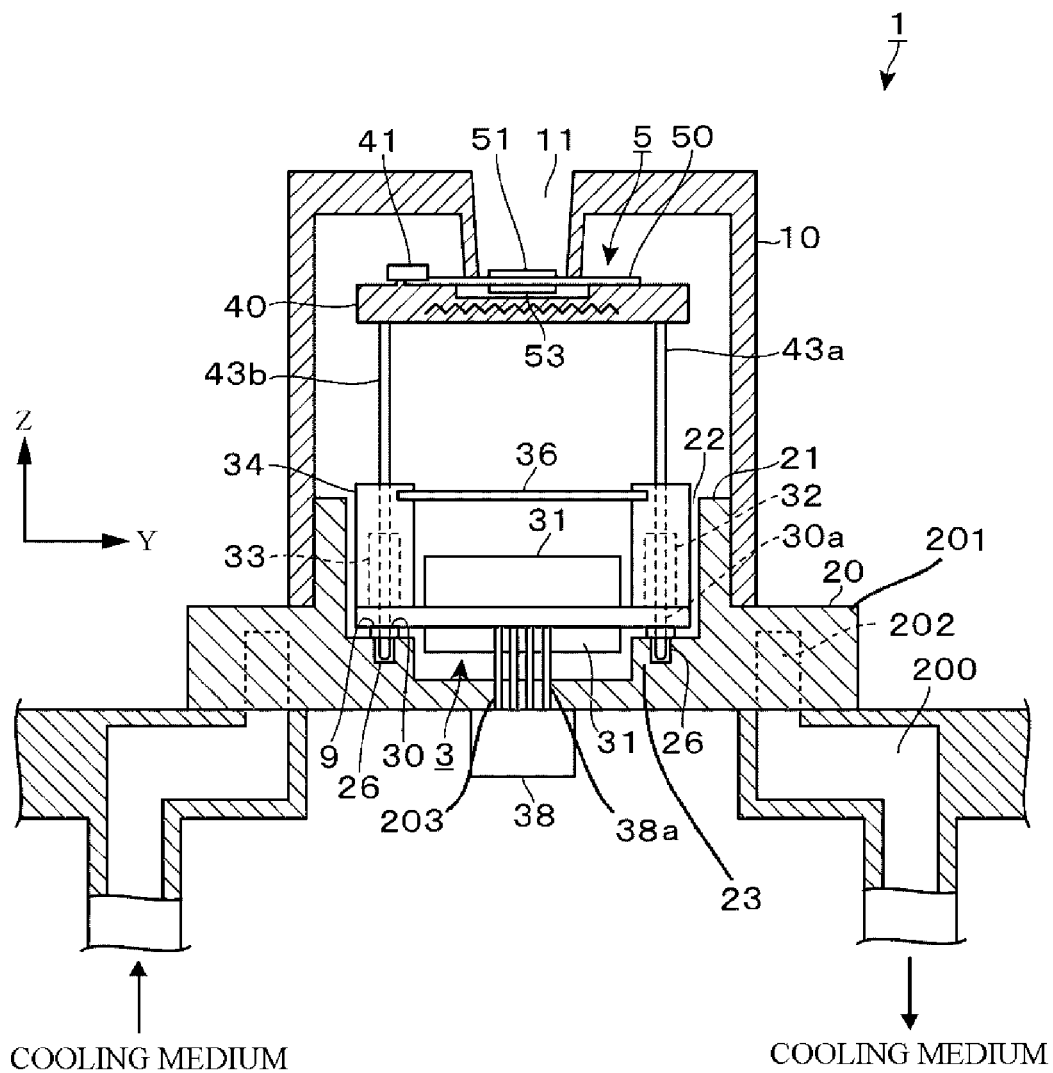
FIG. 2 is a vertical cross-sectional view of the sensing sensor according to the embodiment of the present invention.

The overall configuration of a sensing sensor 1 of the present invention will be described with reference to FIG. 1 and FIG. 2. As illustrated in FIG. 1, the sensing sensor 1 includes a cylindrically-shaped lid portion 10 that has an open lower side, and a base body 20 that covers the lower side of the lid portion 10. As illustrated in FIG. 1 and FIG. 2, the base body 20 is formed of, for example, a nickel-plated copper in a disk shape, and a projecting portion 21 having a circular planar shape is formed in the center of one surface side (upper surface side). The projecting portion 21 is provided with a depressed portion 22 having a rectangular planar shape, and stepped portions 23 that doubly support an oscillator circuit board 3 described below are formed at respective both ends in an X-direction in FIG. 1 on a bottom portion of the depressed portion 22 as illustrated in FIG. 2. The bottom portion of the depressed portion 22 is provided with a hole portion 203 into which a cable 38a connected to a connector 38 described later is inserted as illustrated in FIG. 2. The stepped portions 23 are provided with hole portions 26, into which pins 43a, 43b described later are inserted, at positions corresponding to the respective pins 43a, 43b.

As illustrated in FIG. 1, on the upper surface of the projecting portion 21, two support pillars 24, which are separately disposed in the X-direction, are disposed in each of two rows in a Y-direction across the depressed portion 22. The support pillars 24 have upper ends from which fixing members 25 for fixing a sensor substrate 4 described below each extend upward.

As illustrated in FIG. 2, inside a mounting portion 201 of the base body 20, a refrigerant reservoir 202 to collect a refrigerant flowing through a refrigerant flow channel 200 is disposed. As the refrigerant, for example, a liquid nitrogen is used.

Inside the depressed portion 22, the oscillator circuit board 3 is disposed. As illustrated in FIG. 1, FIG. 2, the oscillator circuit board 3 includes a circuit area 31 that houses an integrated circuit (IC) as a silicon semiconductor element in which oscillator circuit units, such as an oscillator circuit and a regulator, are mounted to respective front surface side and lower surface side of a substrate 30. On both ends in the X-direction of the substrate 30, respective four cylindrical sockets 32, 33 to be electrically connected to the IC in the circuit area 31 are disposed side by side. As illustrated in FIG. 2, at positions corresponding to the respective sockets 32, 33 on the substrate 30, hole portions 30a communicated with the respective sockets 32, 33 are formed. In this example, the six hole portions 30a, in which the sockets 32, 33 are to be disposed, are preliminarily formed on each of both ends in the X-direction of the substrate 30, the sockets 32 are arranged in the two hole portions 30a on each outer side, and the sockets 33 are disposed in the four hole portions 30a in the center side. At one end portion in the Y-axis direction of the oscillator circuit board 3, a cable 38a that electrically connects the connector 38 to the IC in the circuit area 31 is connected to the lower surface side. While FIG. 1 illustrates a drawing in which the cable 38a is connected to the connector 38, the connector 38 is disposed on the lower surface side of the base body 20.

Figure 3:
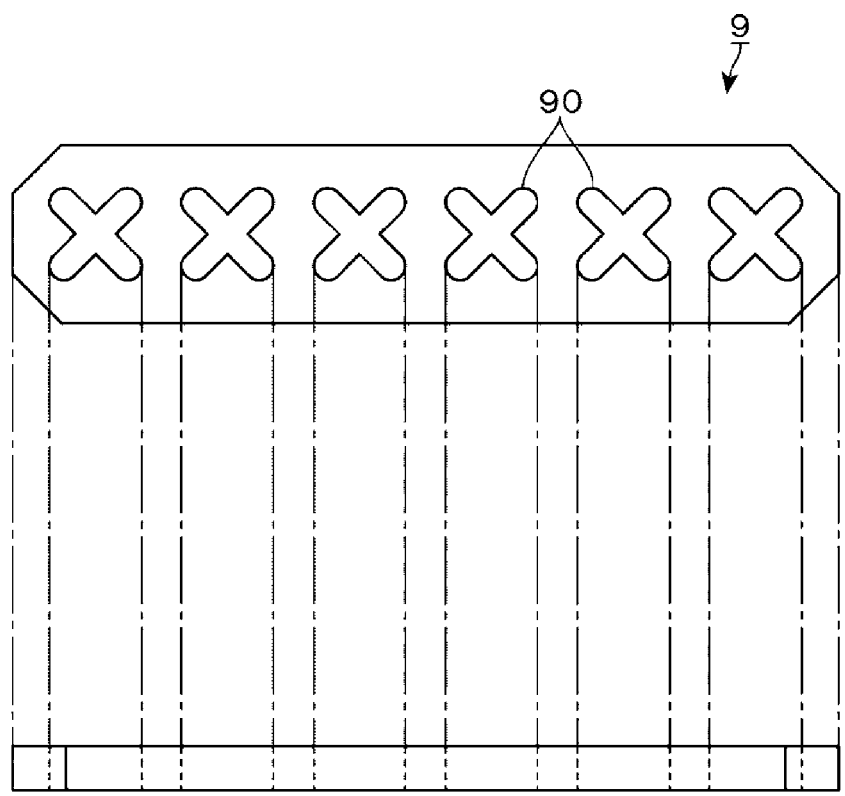
FIG. 3 is a plan view and a side view illustrating a spacer used for the sensing sensor.

The oscillator circuit board 3 is disposed in the depressed portion 22 via spacers 9. As illustrated in FIG. 3, for example, the spacer 9 is formed of Teflon (registered trademark) to a plate-shaped body having a thickness of 0.5 mm, and X-shaped through-hole portions 90 penetrating in the thickness direction are provided. The through-hole portions 90 are formed at positions corresponding to the six hole portions 30a formed at the end portion in the X-direction of the substrate 30.

The spacers 9 are disposed on the upper surfaces of the respective stepped portions 23 such that the positions are each aligned between the through-hole portion 90 and the hole portions 26, and the oscillator circuit board 3 is disposed such that the six hole portions 30a are aligned with the through-hole portions 90. At this time, an outside region separated from the circuit area 31 and regions in which elements, such as switches 60, 61, a heater resistor 64, and the like described later, are disposed on the oscillator circuit board 3 is positioned above the spacer 9.

Return to FIG. 1, FIG. 2, guiding members 34 that each guide the sockets 32, 33 are disposed upward the oscillator circuit board 3. The guiding members 34 are provided with through holes 34a to guide the respective sockets 32, 33. A plate-shaped member 36 is disposed upward the guiding members 34. The plate-shaped member 36 has both ends 36a in the Y-axis direction to which respective hole portions 37 are provided, and is formed to include a region between the both ends 36a expanding in the X-axis direction. The plate-shaped member 36 is pressed onto the guiding members 34 from a Z-axis direction, and the both ends 36a in the Y-direction of the plate-shaped member 36 illustrated in FIG. 1 are each secured to the upper surface of the projecting portion 21 of the base body 20 by a screw member 37a inserted through the hole portion 37. Accordingly, the guiding members 34, the oscillator circuit board 3, and the spacers 9 are internally secured to the depressed portion 22.

Figure 4:
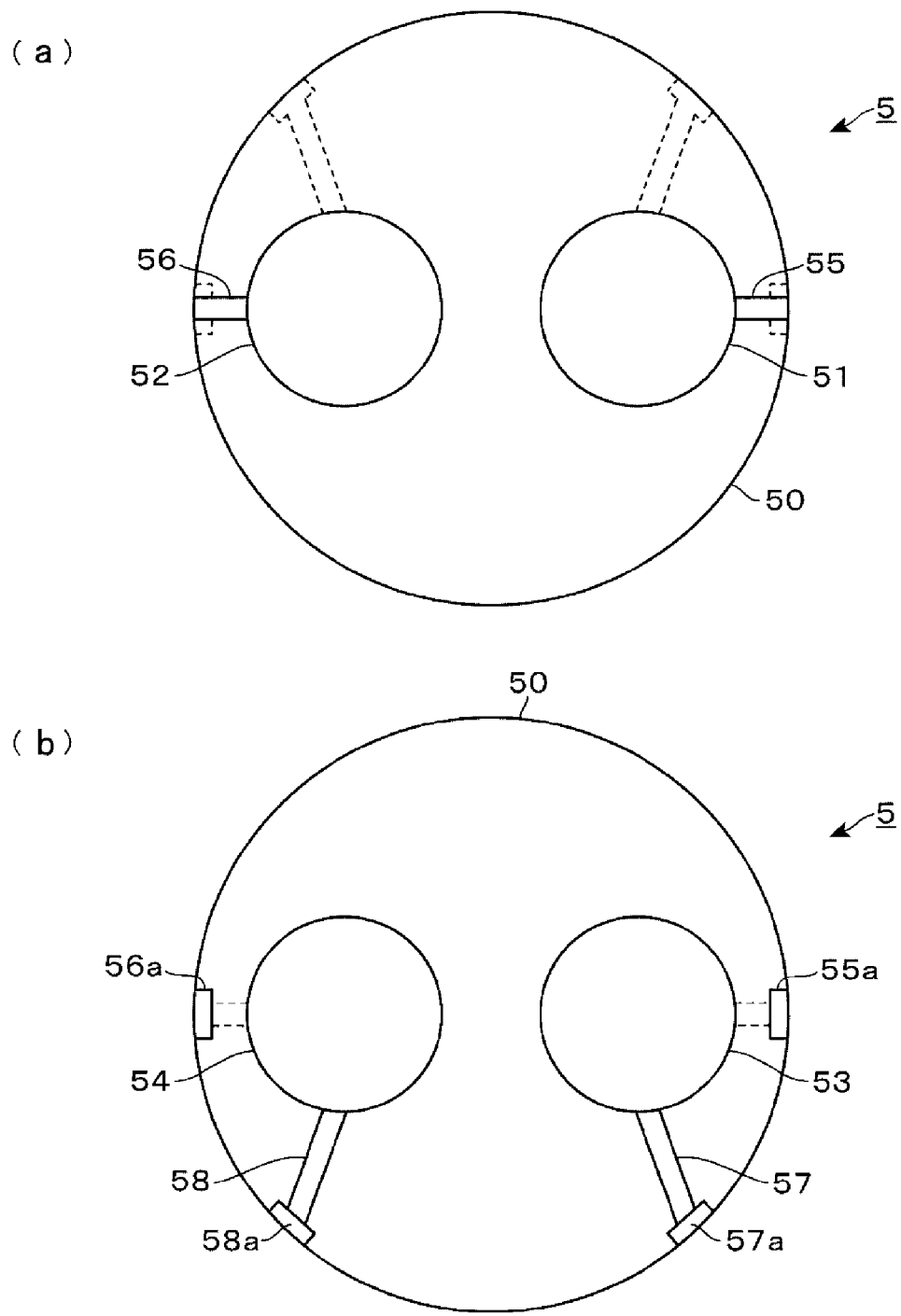
FIG. 4 includes plan views illustrating a front surface side and a back surface side of a crystal resonator used for the sensing sensor.

As illustrated in FIG. 1, the sensor substrate 4 on which a crystal resonator 5 is installed is disposed upward the plate-shaped member 36. As illustrated in FIG. 4, the crystal resonator 5 includes a circular plate-shaped crystal element 50 that is, for example, an AT-cut piezoelectric piece. On an upper surface side ((a) in FIG. 4) and a lower surface side ((b) in FIG. 4) of the crystal element 50, a pair of first excitation electrodes (reaction electrodes) 51, 53 and a pair of second excitation electrodes (reference electrodes) 52, 54, which are each formed of gold (Au) and the like, are disposed to be mutually separated in the Y-axis direction in FIG. 1.

One ends of extraction electrodes 55, 56 are connected to the first and the second excitation electrodes 51, 52 on the upper surface side, respectively, the extraction electrodes 55, 56 are extended to a side surface of the crystal element 50, and terminal portions 55a, 56a are formed at peripheral edge portions of the lower surface. One ends of extraction electrodes 57, 58 are connected to the first and the second excitation electrodes 53, 54 on the lower surface side, respectively, and the extraction electrodes 57, 58 include terminal portions 57a, 58a at peripheral edge portions.

Figure 5:
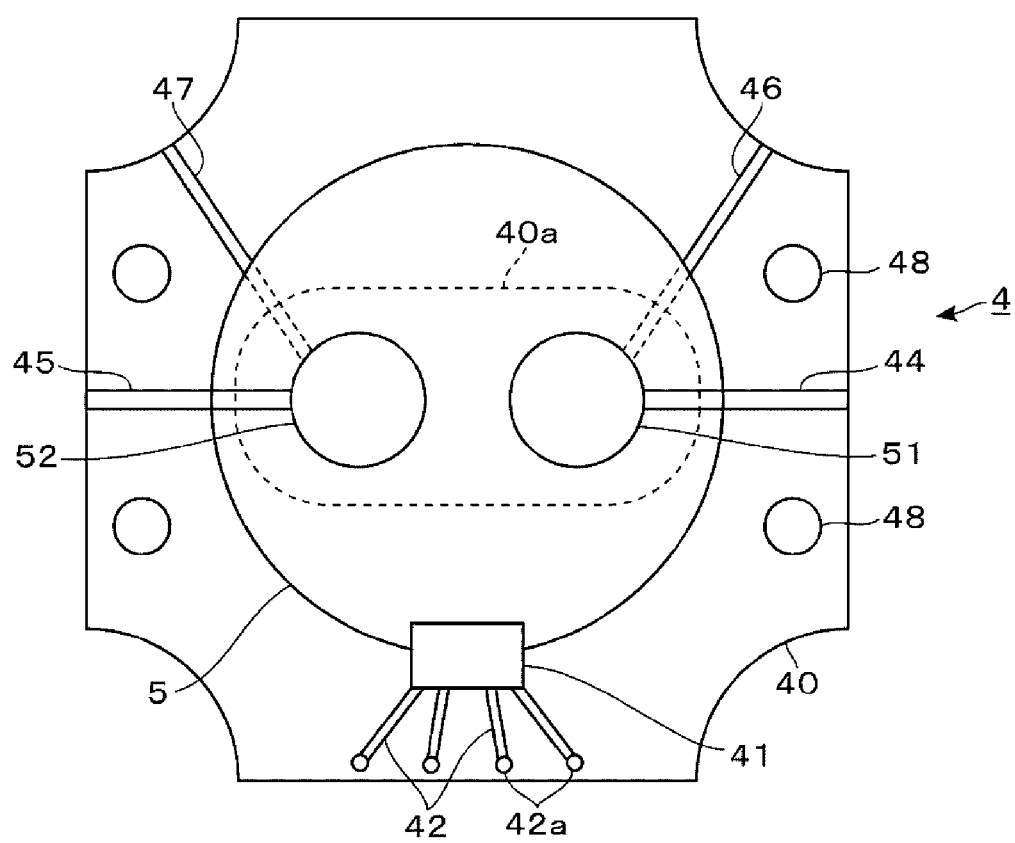
FIG. 5 is a plan view illustrating a sensor substrate on which the crystal resonator is installed.

As illustrated in FIG. 1, FIG. 2, FIG. 5, and FIG. 6, the sensor substrate 4 includes an approximately rectangular substrate 40 as a supporting member. On an upper surface of the substrate 40, an oval depressed portion 40a is provided at a position corresponding to the first and the second excitation electrodes 53, 54 on the lower surface side disposed to the crystal resonator 5. On the upper surface of the substrate 40, wirings 44, 45, 46, and 47 are disposed at positions corresponding to the terminal portions 55a, 56a, 57a, and 58a formed on the lower surface of the crystal resonator 5, respectively. On one end side in the X-axis direction on the lower surface side of the sensor substrate 4 illustrated in FIG. 1, four conductive pins 43a extend downward at positions corresponding to the sockets 32 of the oscillator circuit board 3. On the other end side in the X-axis direction on the lower surface side of the sensor substrate 4, four conductive pins 43b extend downward at positions corresponding to the sockets 33 of the oscillator circuit board 3. The wirings 44, 45, 46, and 47 illustrated in FIG. 5 are extended to the lower surface side via the side surface of the substrate 40, and connected the respective pins 43a.

A heating unit 49 formed of, for example, a heating resistor that heats the crystal resonator 5 is embedded in the substrate 40 of the sensor substrate 4. Furthermore, the sensor substrate 4 includes a temperature detector 41 that detects a temperature of the crystal resonator 5. The heating unit 49 and the temperature detector 41 are extended to the lower surface side of the substrate 40 via wirings 42 and through-holes 42a, and connected to the pins 43b.

Figure 6:
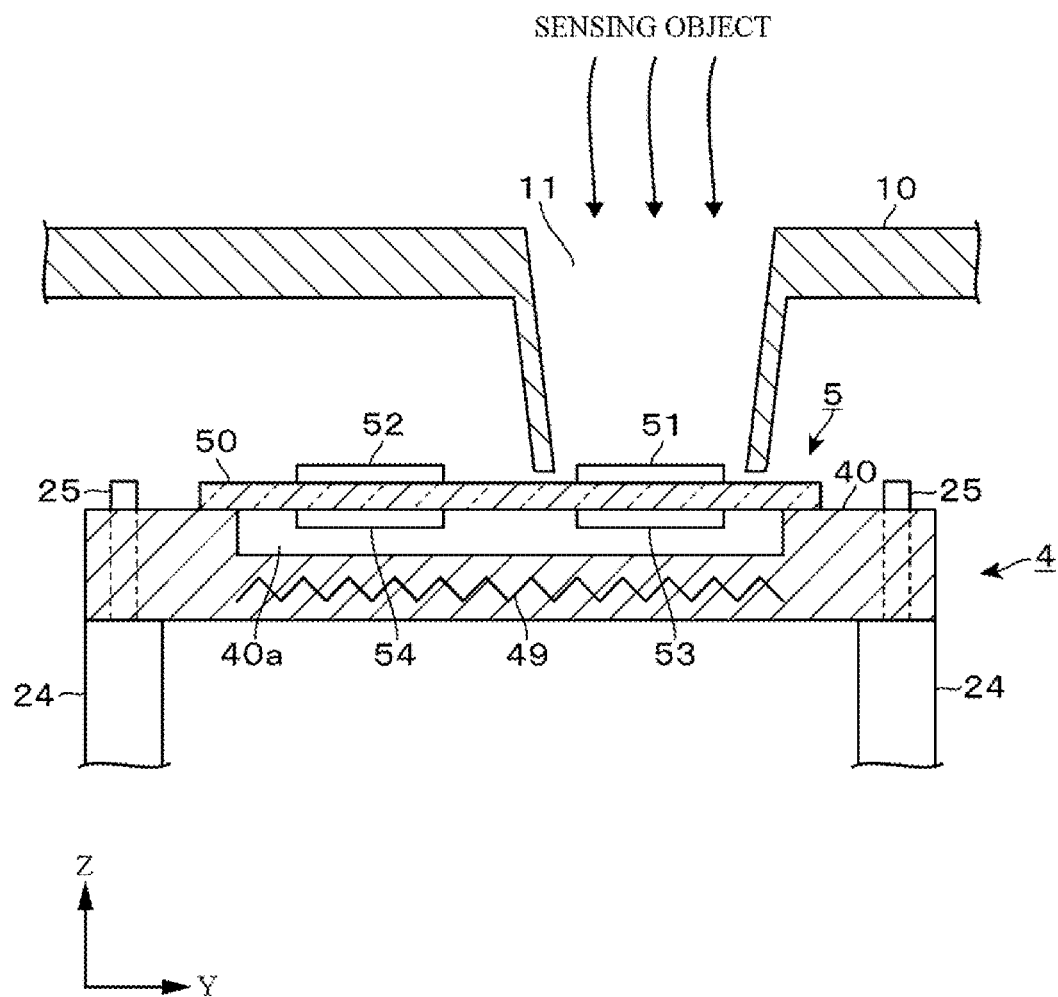
FIG. 6 is a sectional drawing illustrating a part of the sensing sensor.
Figure 7:
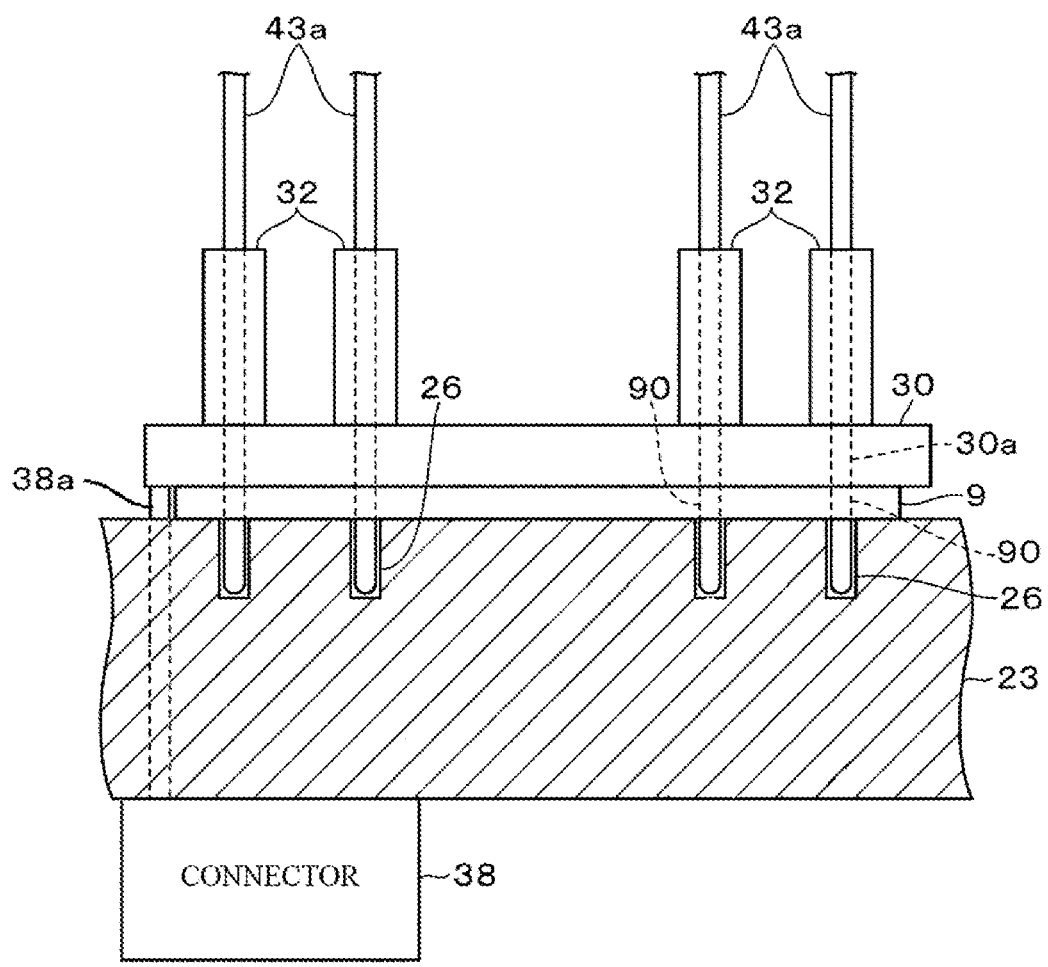
FIG. 7 is a vertical cross-sectional view illustrating a connection of the sensor substrate and an oscillator circuit board to a connector.

Peripheral edge portions in the Y-axis direction of the substrate 40 are provided with hole portions 48 at positions corresponding to the respective fixing members 25 of the support pillars 24. As illustrated in FIG. 6, the sensor substrate 4 is positioned in the X-axis direction and the Y-axis direction by inserting the fixing members 25 through the respective hole portions 48, and the substrate 40 is placed on the upper surfaces of the support pillars 24, thus fixing the height position as illustrated in FIG. 2. At this time, respective pins 43a, 43b are inserted through the through holes 34a of the guiding members 34, and inserted through the corresponding sockets 32, 33. As illustrated in FIG. 7, the respective pins 43a are inserted through the sockets 32, thus being electrically connected. Distal ends of the pins 43a are inserted through the hole portions 30a formed in the substrate 30 and the through-hole portions 90 formed in the spacers 9, thus being inserted into the respective hole portions 26 formed in the stepped portions 23. The cable 38a connected to the oscillator circuit board 3 is extended downward the base body 20 via the hole portion 203 formed in the base body 20, thus being connected to the connector 38. Accordingly, the crystal resonator 5 disposed on the substrate 40, the circuit area 31, and the connector 38 are mutually electrically connected.

As illustrated in FIG. 2, when the sensor substrate 4 is mounted to the base body 20, the lid portion 10 is disposed to cover the upper portion of the sensor substrate 4 and surround the peripheral area of the projecting portion 21, thus engaging the lid portion 10 with the base body 20. At a position biased to the one end side in the Y-axis direction on the upper surface of the lid portion 10, as illustrated in FIG. 2, a cone-shaped opening portion 11 is provided. As illustrated in FIG. 6, the arrangement is that the first excitation electrode 51 on the upper surface side of the crystal resonator 5 faces the opening portion 11 when the lid portion 10 is engaged with the base body 20. At this time, the lower end of the opening portion 11 is separated from the surface of the crystal resonator 5 by 0.5 mm.

Figure 8:
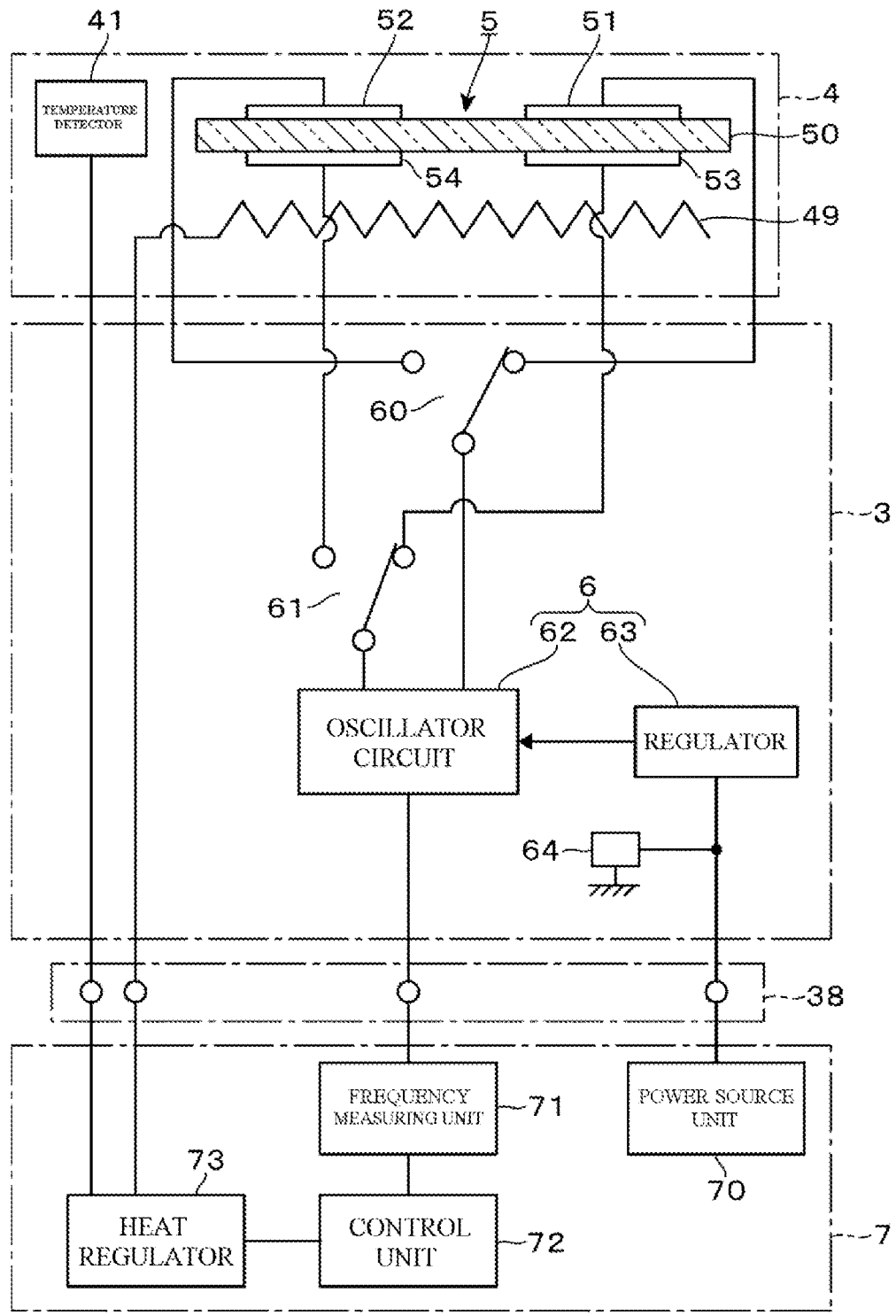
FIG. 8 is a schematic configuration diagram illustrating a sensing device connected to the sensing sensor.

Next, the overall configuration of a sensing device connected to the sensing sensor 1 will be described. As illustrated in FIG. 8, the oscillator circuit board 3 includes an oscillator circuit 62 and a regulator 63 that regulates a voltage supplied to the oscillator circuit 62, and the oscillator circuit 62 and the regulator 63 are disposed in the circuit area 31. The oscillator circuit 62 and the regulator 63 correspond to an oscillator circuit unit 6. By connecting the sensor substrate 4 to the oscillator circuit board 3, the first and the second excitation electrodes 51, 52 on the upper surface side of the crystal resonator 5 are connected to the oscillator circuit 62 via a switch 60 disposed on the oscillator circuit board 3. The first and the second excitation electrodes 53, 54 on the lower surface side of the crystal resonator 5 are connected to the oscillator circuit 62 via a switch 61 disposed on the oscillator circuit board 3.

The sensing sensor 1 is connected to a main unit 7 via the connector 38. The main unit 7 includes, for example, a power source unit 70 that supplies a driving voltage to the oscillator circuit 62 disposed to the sensing sensor 1, and a frequency measuring unit 71 that measures a frequency output from the oscillator circuit 62. The frequency signal measured by the frequency measuring unit 71 is input to a control unit 72 in the configuration. The main unit 7 includes a heat regulator 73 that regulates an output of the heating unit 49 based on a temperature detection value detected by the temperature detector 41, thus regulating the temperature of the crystal resonator 5. The control unit 72 is configured to adjust a set temperature of the heat regulator 73 to increase the temperature of the crystal resonator 5 from −190° C., which is a temperature given by cooling by the liquid nitrogen, at a rate of 1° C./1 minute.

By connecting the main unit 7 to the sensing sensor 1, the power source unit 70 is connected to the regulator 63. Thus, for example, the 5-V voltage output from the power source unit 70 is regulated by the regulator 63 to become the 3-V voltage, and applied to the oscillator circuit 62. The oscillator circuit board 3 includes a heater resistor 64, which is a heater circuit that heats the oscillator circuit 62, having an electrical resistance of, for example, 330 g. The heater resistor 64 is connected in parallel with the regulator 63, and generates heat with the 5-V voltage output from the power source unit 70. The heater resistor 64 heats the oscillator circuit 62 and the regulator 63 (oscillator circuit unit 6) disposed in the circuit area 31.

By connecting the sensing sensor 1 to the main unit 7, the frequency measuring unit 71 is connected to the oscillator circuit 62. The sensing sensor 1 of the present invention switches the excitation electrodes connected to the oscillator circuit 62 between the reaction electrode side (first excitation electrodes 51, 53) and the reference electrode side (second excitation electrode 52, 54) by switching the switch 60 and the switch 61. Accordingly, the frequency measuring unit 71 measures each of a first oscillation frequency F1 of the reaction electrode side and a second oscillation frequency F2 of the reference electrode side.

Then, when a gas containing a sensing object is supplied toward the sensing sensor 1, since the sensing object adheres to the excitation electrode 51 of the reaction electrode side facing the opening portion 11 on the upper surface side, the first oscillation frequency F1 significantly varies corresponding to the amount of the sensing object. The control unit 72 stores a relationship between a difference between the first oscillation frequency F1 of the first excitation electrodes 51, 53 of the reaction electrode side and the second oscillation frequency F2 of the second excitation electrodes 52, 54 of the reference electrode side, which are preliminarily measured, and the amount (mass) of the sensing object. Then, from the difference between the first oscillation frequency F1 and the second oscillation frequency F2 measured by the frequency measuring unit 71, the amount of the sensing object corresponding to the difference is detected.

Subsequently, operations of the sensing sensor 1 according to the embodiment of the present invention will be described. First, the main unit 7 is connected to the connector 38 of the sensing sensor 1, and furthermore, the liquid nitrogen is flown through the refrigerant flow channel 200. Thus, the base body 20 is cooled to, for example, −190° C. At this time, the sensor substrate 4 is cooled via the pins 43a, 44b and the support pillars 24, and cooled to, for example, −184° C. Therefore, the pins 43a, 44b and the support pillars 24 correspond to heat transfer members. In the state where the crystal resonator 5 is cooled by the liquid nitrogen, the gas as the sensing object is supplied toward the opening portion 11 of the sensing sensor 1. At this time, the supplied gas contacts the first excitation electrode 51 of the reaction electrode side facing the bottom portion of the opening portion 11, thereby being cooled to adhere.

Subsequently, the switches 60, 61 are switched by time division, and the temperature of the heating unit 49 is gradually increased at, for example, 1° C./1 minute while measuring the oscillation frequency F1 of the reaction electrode side (first excitation electrodes 51, 53) and the oscillation frequency F2 of the reference electrode side (second excitation electrodes 52, 54) by the control unit 72. Gradually heating the crystal resonator 5 causes the sensing object adhered to the first excitation electrode 51 to be desorbed. At this time, when desorbing from the first excitation electrode 51, the oscillation frequency F1 of the first excitation electrodes 51, 53 of the reaction electrode side significantly varies. Meanwhile, since the sensing object does not adhere to the second excitation electrodes 52, 54 of the reference electrode side, the mass change does not occur when the temperature is increased, and the oscillation frequency F2 hardly varies.

The control unit 72 obtains a timing of the gas desorption through an observation of the oscillation frequencies F1, F2, and detects the mass of the sensing object based on the difference between the first oscillation frequency F1 and the second oscillation frequency F2. While the temperature detector 41 always detects the temperature, the temperature at the timing is detected as a desorption temperature of the sensing object. Based on the thus detected desorption temperature, the kind of the sensing object can be specified.

While the detection of the gas as the sensing object is thus performed, in the above-described embodiment, the oscillator circuit board 3 is doubly supported upward the Teflon spacers 9 disposed on the upper surface of the stepped portion 23 of the base body 20. Therefore, the heat conduction between the base body 20 and the oscillator circuit board 3 is reduced by the spacers 9. Consequently, the oscillator circuit board 3 and the circuit area 31 disposed to the oscillator circuit board 3 have the temperatures provided by the cooling higher than the temperature of the base body 20.

By a power-on of the power source unit 70, the voltage regulated to 3 V via the regulator 63 is applied to the oscillator circuit 62. Then, the oscillator circuit 62 is driven to cause the crystal resonator 5 to oscillate. At this time, the voltage applied from the power source unit 70 is applied to also the heater resistor 64, and the heater resistor 64 generates heat.

Figure 9:
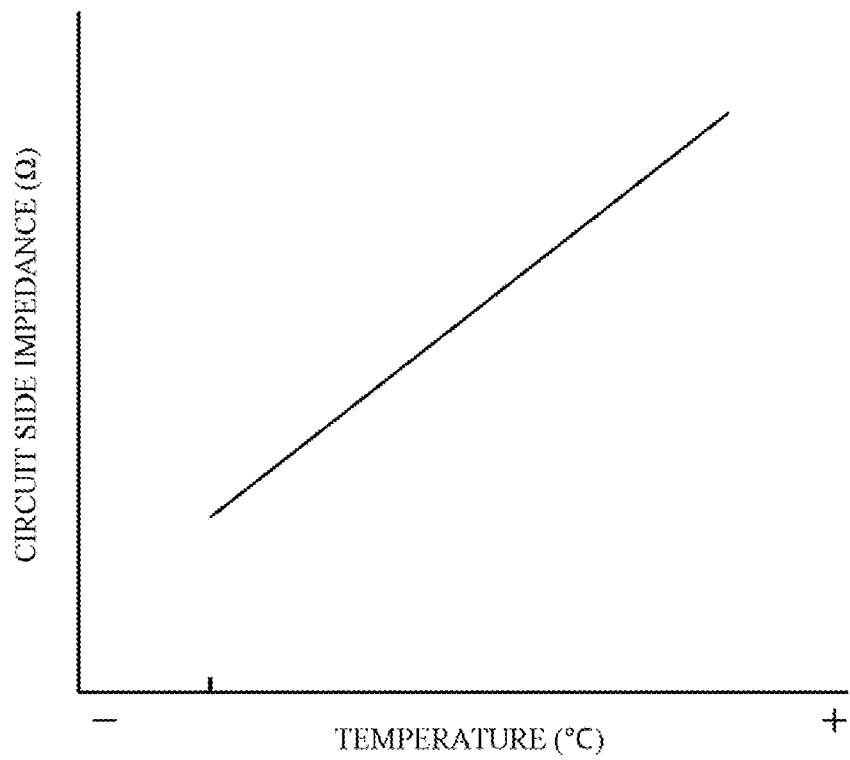
FIG. 9 is a characteristic diagram illustrating a relationship between a temperature and impedance of an oscillator circuit.

As illustrated in FIG. 9, the oscillator circuit 62 has a negative resistance increased by decreasing the temperature. While the sensing sensor 1 of the present invention causes the sensing object to adhere to the crystal resonator 5 and detects the sensing object based on the amount of frequency variation as described above, since the adhesion of the material increases a CI value, a frequency range in which the crystal resonator 5 normally oscillates is narrowed. Therefore, from an aspect of expanding the measurable frequency range, the negative resistance of the oscillator circuit 62 side is preferably increased, and the temperature is preferably decreased.

Figure 10:
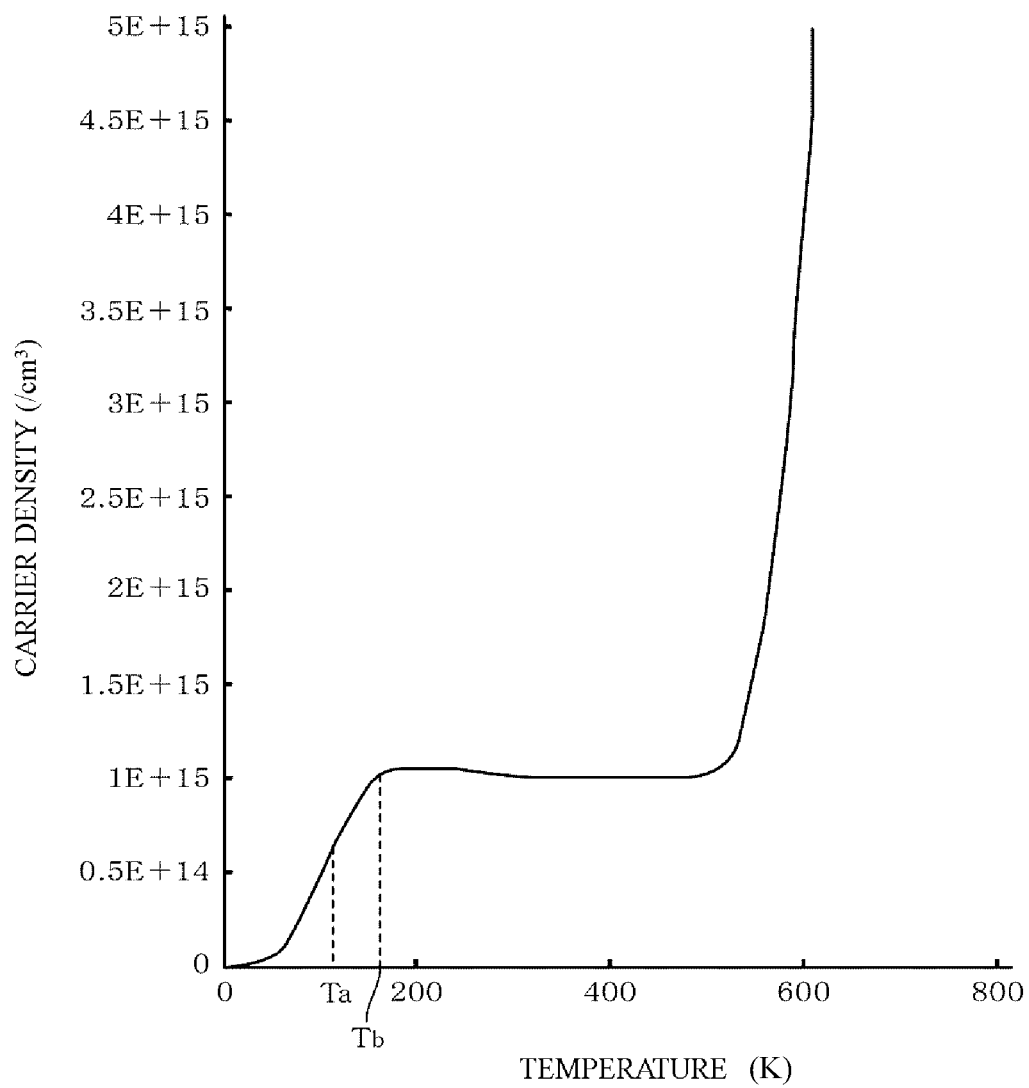
FIG. 10 is a characteristic diagram illustrating a relationship between a temperature and a carrier density of a semiconductor element.

Here, for example, the semiconductor element formed of silicon has a carrier density that varies depending on the temperature as illustrated in FIG. 10. The carrier density indicates a conductivity of the semiconductor element, and increasing the carrier density increases the conductivity and decreasing the carrier density increases an insulation property. While the silicon semiconductor element keeps the stable carrier density in a temperature zone from −110° C. (163 K) to 300° C. (573 K), the carrier density gradually decreases when the temperature falls below Tb, for example, a temperature about −110° C. When the temperature further decreases to fall below a temperature Ta at which the carrier density becomes excessively low, the insulation property of the semiconductor element is excessively enhanced, thus falling below a functional limit temperature. Therefore, the circuit area 31 that forms the oscillator circuit 62 and the regulator 63 (oscillator circuit unit 6) stop the function, and the oscillation stops. Accordingly, in combination with the above-described aspect of increasing the negative resistance, the circuit area 31 is preferably controlled to a temperature that is a cryogenic temperature and equal to or more than the functional limit temperature of the semiconductor element. The temperature that is the cryogenic temperature and equal to or more than the functional limit temperature of the semiconductor element is a temperature in the temperature zone lower than the temperature Tb, which is a temperature at which the carrier density decreases to sufficiently increase the negative resistance of the oscillator circuit, and higher than the temperature Ta at which the semiconductor element cannot maintain the function. Specifically, in the case of the silicon semiconductor, it is approximately from −170° C. (103 K) to −110° C. (163 K).

The temperature of the liquid nitrogen used as a cooling medium in the above-described embodiment is −196° C. As described in the embodiment below, in a case of a sensing sensor 1 configured similarly to the sensing sensor 1 described in the above-described embodiment excluding that the spacer 9 and the heater resistor 64 are removed, the temperature of the oscillator circuit board 3 decreases to −184° C., and the oscillator circuit unit 6 stops. In contrast, in the sensing sensor 1 described in the above-described embodiment, the spacer 9 cuts off the heat conduction, thus reducing the cooling of the oscillator circuit unit 6. Furthermore, since the heater resistor 64 generates heat, the oscillator circuit 62 and the regulator 63 (oscillator circuit unit 6) disposed on the oscillator circuit board 3 are heated. The circuit area 31 that includes the ICs, such as the oscillator circuit 62 and the regulator 63, is cooled to the cryogenic temperature by the liquid nitrogen while being kept to the temperature, for example, about −160° C. in combination with the reduction of the cooling by the spacer 9 and the heating by the heater resistor 64. Accordingly, as described in the embodiment below, the temperature of the oscillator circuit unit 6 can be controlled to a temperature in the temperature zone of the cryogenic temperature in which the negative resistance of the oscillator circuit unit 6 increases while ensuring the normal operation of the oscillator circuit unit 6.

In this embodiment, since the temperature of the oscillator circuit unit 6 is kept to the temperature about −160° C. and the negative resistance of the oscillator circuit unit 6 is increased, the measuring range in the frequency measurement is expanded and the range of the detection of the sensing object by the sensing sensor 1 is expanded. Furthermore, the oscillator circuit unit 6 is controlled to the temperature zone in which the oscillator circuit unit 6 normally oscillates without stopping. Accordingly, the crystal resonator 5 can be stably oscillated even when the CI value of the crystal resonator 5 increases due to the adhesion of the sensing object to the excitation electrode 51 of the reaction electrode side on the upper surface side.

According to the above-described embodiment, in the sensing sensor 1 that attaches the sensing object to the crystal resonator 5 to detect the sensing object, the spacer 9 is disposed between the oscillator circuit unit 6 that oscillates the crystal resonator 5 and the base body 20 that cools the oscillator circuit 62 to the cryogenic temperature, and the heater resistor 64 that heats the oscillator circuit unit 6 is disposed on the oscillator circuit board 3. Therefore, the temperature of the oscillator circuit unit 6 can be a temperature that does not fall below the functional limit temperature of the silicon semiconductor and is a low temperature as much as possible. Accordingly, the negative resistance of the oscillator circuit unit 6 can be increased, thereby ensuring the expanded measurement dynamic range and the stable oscillation of the crystal resonator 5.

The temperature that does not fall below the functional limit temperature and is a low temperature as much as possible is preferably −170° C. to −110° C. when the main material of the semiconductor element constituting the oscillator circuit unit 6 is silicon.

The pins 43a, 43b that extend from the sensor substrate 4 to be electrically conducted with the oscillator circuit board 3 have the distal ends configured to contact the base body 20, and the contacted area is configured to be reduced while having electrical conduction between the oscillator circuit board 3 and the pins 43a, 43b. Therefore, the heat conduction from the oscillator circuit board 3 side to the pins 43a, 43b can be reduced, and the pins 43a, 43b can be cooled by the base body 20, thus ensuring suppression of the temperature rise of the sensor substrate 4.

Figure 11:
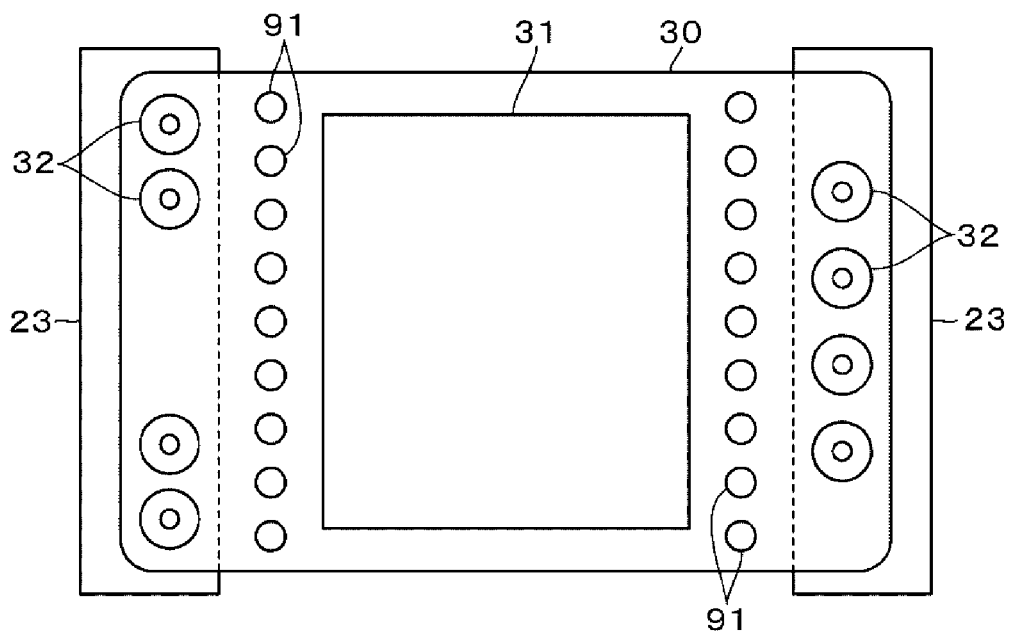
FIG. 11 is a plan view illustrating another example of a heat insulating portion according to the embodiment of the present invention.

Another example of the embodiment of the present invention will be described. For example, instead of the use of the spacer 9, a region of the oscillator circuit board 3 outside with respect to the installation region of the circuit area 31 may be disposed upward the stepped portion 23, and the heat conduction between a region of the substrate 30 upward the stepped portion 23 and the installation region of the circuit area 31 may be suppressed. For example, as illustrated in FIG. 11, through-holes 91 (through-hole portion) are provided in rows between the installation region of the circuit area 31 of the substrate 30 used for the oscillator circuit board 3 and the regions of the substrate 30 upward the stepped portions 23. This narrows a cross-sectional area of a portion between the region side upward the stepped portion 23 and the installation region of the circuit area 31, the heat conduction is reduced, and the installation region of the circuit area 31 is less likely to be cooled, thereby providing the similar effect. The spacer 9 may be disposed between the stepped portion 23 and the oscillator circuit board 3 together with the oscillator circuit board 3 illustrated in FIG. 11. Instead of forming the through-holes 91 in rows, through-holes, such as slits, may be provided.

Embodiment

To verify the effect of the embodiment of the present invention, as the embodiment, the sensing sensor 1 illustrated in FIG. 1 to FIG. 8 was used, the liquid nitrogen was flown through the base body 20 to perform the cooling, subsequently, the oscillator circuit 62 was driven, and the temperature of the region of the oscillator circuit board 3 in which the circuit area 31 was disposed was measured. Whether the stop of the oscillator circuit 62 during the driving of the oscillator circuit 62 was confirmed or not was observed.

An example in which a process similar to that of the embodiment was performed using a sensing sensor configured similarly to that in the embodiment excluding that the heater resistor 64 was not disposed was defined as a comparative example 1.

Furthermore, an example in which a process similar to that of the embodiment was performed using a sensing sensor configured similarly to that in the comparative example 1 excluding that the spacer 9 was removed and the oscillator circuit board 3 was disposed on the upper surface of the stepped portion 23 was defined as a comparative example 2.

Table 1 indicates the result, and indicates, in the embodiment and the comparative examples 1 and 2, the temperature of the oscillator circuit board 3 ten minutes after the power-on of the oscillator circuit 62, and whether the stop of the oscillation of the oscillator circuit unit 6 was confirmed in ten minutes after the power-on of the oscillator circuit unit 6 or not.

TABLE 1

| | OSCILLATOR CIRCUIT BOARD TEMPERATURE (° C.) | OSCILLATION STOP YES/NO |
|---|---|---|
| EMBODIMENT | −164.0 | NO |
| COMPARATIVE EXAMPLE 1 | −173.4 | YES |
| COMPARATIVE EXAMPLE 2 | −184.1 | YES |

As indicated in Table 1, in both the comparative examples 1 and 2, the temperature of the oscillator circuit board 3 was −170° C. or less, and the stop of the oscillator circuit unit 6 was confirmed. In contrast, in the embodiment, the temperature of the oscillator circuit board 3 increased to −164° C., and the stop of the oscillator circuit unit 6 was not confirmed. Accordingly, it can be said that, according to the present invention, the temperature of the oscillator circuit unit 6 can be made to be the temperature that does not fall below the functional limit temperature and is a low temperature as much as possible, the negative resistance of the oscillator circuit unit 6 can be increased, and the measurement dynamic range can be expanded.

In the sensing sensor 1 according to the embodiment, in the measurement of the temperature rise of the crystal resonator 5 after the driving start of the oscillator circuit unit 6, the temperature was −191° C. immediately after the power-on of the oscillator circuit 62, and −187° C. also ten minutes later. Accordingly, it can be said that also in the case where the heater resistor 64 that heats the oscillator circuit unit 6 was disposed, the temperature rise in the crystal resonator 5 was sufficiently reduced to hardly have an influence.

The invention claimed is:

1. A sensing sensor that attaches a substance to be sensed to a piezoelectric resonator, detaches the substance to be sensed by changing a temperature of the piezoelectric resonator, and senses the substance to be sensed based on a relationship between a change of an oscillation frequency and the temperature of the piezoelectric resonator, the substance to be sensed being a gas, the sensing sensor comprising:
    a base body, cooled by a liquid nitrogen;
    the piezoelectric resonator, cooled by the base body;
    a heating unit that heats the piezoelectric resonator for changing the temperature of the piezoelectric resonator;
    a substrate mounted to the base body, the substrate including an oscillator circuit unit and a heater circuit thereon, the oscillator circuit unit oscillating the piezoelectric resonator, the heater circuit heating the oscillator circuit unit; and
    a heat insulating portion, disposed between the base body and the oscillator circuit unit for avoiding a heat transfer of a cool heat from the base body to the oscillator circuit unit via the substrate.

2. The sensing sensor according to claim 1, wherein
the oscillator circuit unit includes a semiconductor element containing a silicon, and
the oscillator circuit unit has a temperature controlled to from −170° C. to −110° C.

3. The sensing sensor according to claim 1, wherein
the heat insulating portion is a spacer with a heat insulating property disposed between the substrate and the base body.

4. The sensing sensor according to claim 1, wherein
in the substrate, a region on which the oscillator circuit unit is disposed is separated from the base body, and a region outside with respect to the region contacts the base body, and
the heat insulating portion is a through-hole portion formed in the substrate.

5. The sensing sensor according to claim 1, wherein
the piezoelectric resonator is supported by a supporting member at a position on an opposite side of the base body with respect to the oscillator circuit unit, and
the supporting member and the base body are mutually connected by a heat transfer member that transfers a heat of the piezoelectric resonator to the base body.

* * * * *